US010878511B1

(12) United States Patent
Allen

(10) Patent No.: US 10,878,511 B1
(45) Date of Patent: *Dec. 29, 2020

(54) MERCHANT PORTAL SYSTEM WITH EXPLANATION OF BENEFITS

(71) Applicant: VPay, Inc., Plano, TX (US)

(72) Inventor: Robert M. Allen, Plano, TX (US)

(73) Assignee: VPay, Inc., Plano, TX (US)

( * ) Notice: Subject to any disclaimer, the term of this patent is extended or adjusted under 35 U.S.C. 154(b) by 324 days.

This patent is subject to a terminal disclaimer.

(21) Appl. No.: 16/051,768

(22) Filed: Aug. 1, 2018

Related U.S. Application Data

(63) Continuation of application No. 14/833,853, filed on Aug. 24, 2015, now Pat. No. 10,068,295, which is a continuation-in-part of application No. 13/709,717, filed on Dec. 10, 2012, now Pat. No. 9,117,207, which is a continuation of application No. 13/495,492, filed on Jun. 13, 2012, now Pat. No. 8,332,238.

(60) Provisional application No. 61/653,175, filed on May 30, 2012.

(51) Int. Cl.
*G06Q 40/08* (2012.01)
*G16H 40/20* (2018.01)
*G06Q 20/14* (2012.01)
*G06Q 20/10* (2012.01)

(52) U.S. Cl.
CPC ............ *G06Q 40/08* (2013.01); *G06Q 20/10* (2013.01); *G06Q 20/14* (2013.01); *G16H 40/20* (2018.01)

(58) Field of Classification Search
CPC .................................................... G06Q 40/08
See application file for complete search history.

(56) References Cited

U.S. PATENT DOCUMENTS

| 4,491,725 | A | * | 1/1985 | Pritchard ............. G06Q 20/102 705/2 |
| 6,188,766 | B1 | | 2/2001 | Kocher |
| 6,343,310 | B1 | | 1/2002 | DiRienzo |
| 6,901,387 | B2 | | 5/2005 | Wells et al. |
| 7,072,842 | B2 | | 7/2006 | Provost et al. |
| 7,229,011 | B2 | | 6/2007 | Hansen et al. |
| 7,246,068 | B2 | | 7/2007 | Thomas, Jr. |

(Continued)

OTHER PUBLICATIONS

Shingles, et al., "Next Phase of Medical Management Systems: Automating Administrative Transactions to Integrate Payors and Providers", JHIM: Journal of Healthcare Information Management, Feb. 2001, vol. 15, No. 3, pp. 223-235.

(Continued)

*Primary Examiner* — Eric T Wong
(74) *Attorney, Agent, or Firm* — Andriv T. Lytvyn; Anton J. Hopen; Smith & Hopen, P.A.

(57) ABSTRACT

A method for facilitating the delivery of electronic funds and conveying an explanation of benefits (EOB) to a service provider is described herein. A claim for payment by a service provider (such as a physician's office) is adjudicated by a third party administrator which authorizations payment in an amount and also provides an EOB explaining the payment authorization. A virtual payment card is generated and transmitted to the provider or the merchant acquirer for the provider. When the service provider logs into its merchant portal to view and reconcile payment card deposits, the EOB is viewable with its associated payment deposit record.

15 Claims, 6 Drawing Sheets

(56) References Cited

U.S. PATENT DOCUMENTS

| | | | |
|---|---|---|---|
| 7,383,223 B1 | 6/2008 | Dilip et al. | |
| 7,434,729 B2 | 10/2008 | Cracchiolo et al. | |
| 7,548,641 B2 * | 6/2009 | Gilson | G06Q 20/04 |
| | | | 382/137 |
| 7,590,557 B2 | 9/2009 | Harrison et al. | |
| 7,792,686 B2 | 9/2010 | Allen | |
| 7,792,749 B2 | 9/2010 | Ganesan | |
| 7,853,524 B2 | 12/2010 | Kight et al. | |
| 7,895,119 B2 | 2/2011 | Praisner | |
| 7,925,518 B2 * | 4/2011 | Lee | G06Q 20/346 |
| | | | 705/2 |
| 7,958,049 B2 | 6/2011 | Jamison et al. | |
| 7,970,629 B2 | 6/2011 | Christen | |
| 8,060,382 B1 * | 11/2011 | Lee | G06Q 50/22 |
| | | | 705/3 |
| 8,332,238 B1 * | 12/2012 | Allen | G06Q 20/0425 |
| | | | 705/2 |
| 9,117,207 B2 * | 8/2015 | Allen | G06Q 40/02 |
| 10,068,295 B1 * | 9/2018 | Allen | G16H 40/67 |
| 2002/0072942 A1 | 6/2002 | Kuykendall et al. | |
| 2002/0077837 A1 | 6/2002 | Krueger et al. | |
| 2002/0198831 A1 * | 12/2002 | Patricelli | G06Q 20/10 |
| | | | 705/40 |
| 2004/0172312 A1 | 9/2004 | Selwanes et al. | |
| 2005/0086075 A1 | 4/2005 | Kaehler et al. | |
| 2005/0102170 A1 | 5/2005 | Lefever et al. | |
| 2005/0108153 A1 | 5/2005 | Thomas et al. | |
| 2005/0122953 A1 | 6/2005 | Ilic | |
| 2005/0209964 A1 | 9/2005 | Allen et al. | |
| 2007/0005402 A1 | 1/2007 | Kennedy et al. | |
| 2007/0038484 A1 * | 2/2007 | Hoffner | G06Q 40/08 |
| | | | 705/4 |
| 2007/0168283 A1 | 7/2007 | Alvarez et al. | |
| 2007/0260969 A1 | 11/2007 | Fetzer | |
| 2008/0010096 A1 | 1/2008 | Patterson et al. | |
| 2008/0059223 A1 * | 3/2008 | Lu | G06Q 40/02 |
| | | | 705/2 |
| 2008/0086420 A1 | 4/2008 | Gilder et al. | |
| 2008/0140447 A1 | 6/2008 | Pourfallah et al. | |
| 2008/0281641 A1 | 11/2008 | Pilzer et al. | |
| 2009/0037333 A1 | 2/2009 | Flitcroft et al. | |
| 2009/0138277 A1 * | 5/2009 | Warren | G06Q 10/10 |
| | | | 705/2 |
| 2010/0030580 A1 | 2/2010 | Salwan | |
| 2010/0185466 A1 | 7/2010 | Paradis et al. | |
| 2010/0205078 A1 | 8/2010 | Lawrence et al. | |
| 2011/0087598 A1 | 4/2011 | Bozeman | |
| 2011/0178816 A1 | 7/2011 | Lee et al. | |
| 2011/0184857 A1 | 7/2011 | Shakkarwar | |
| 2011/0258004 A1 * | 10/2011 | Dean | G06Q 10/10 |
| | | | 705/4 |
| 2012/0095787 A1 * | 4/2012 | Davis | G06F 19/328 |
| | | | 705/4 |
| 2012/0185271 A1 * | 7/2012 | Warren | G06Q 20/10 |
| | | | 705/2 |
| 2012/0215563 A1 * | 8/2012 | Lassen | G06Q 50/22 |
| | | | 705/3 |
| 2012/0253989 A1 * | 10/2012 | Otruba | G06Q 20/351 |
| | | | 705/27.1 |
| 2012/0323596 A1 * | 12/2012 | VerHulst | G06Q 50/22 |
| | | | 705/2 |
| 2013/0110539 A1 * | 5/2013 | Sohr | G06Q 50/22 |
| | | | 705/2 |
| 2014/0297304 A1 * | 10/2014 | Nguyen | G06Q 20/10 |
| | | | 705/2 |

OTHER PUBLICATIONS

Brousseau, "IBML and the Move Toward Healthcare Electronification", Today, TAWPI, Mar./Apr. 2009, pp. 8-10.

Baker, "Persistence Pays When Posting Payments", Lockbox Payments, Today, TAWPI, Nov./Dec. 2009, pp. 22-23.

Credit Cards, Rising Interchange Fees Have Increased Costs for Merchants, but Options for Reducing Fees Pose Challenges, Highlights of GAO-10-45, Nov. 2009.

Visa's Global Registry of Service Providers—Independent Sales Organizations and Encryption Support Organizations as of Mar. 1, 2012, Visa Inc. 2010, pp. 1-53.

MasterCard Worldwide U.S. and Interregional Interchange Rates, Rates and Criteria Effective as of Oct. 2011, MasterCard 2011, pp. 1-170.

The Payment Card Economics Review, The Industry and Its Legal Challenges, An occasional publication of payingwithplastic.org., Winter 2004, vol. 2, pp. 1-224.

Levitin, Priceless? The Social Costs of Credit Card Merchant Restraints, Harvard Journal on Legislation, 2008, vol. 45, pp. 1-58.

The Anatomy of a Transaction, MasterCard Worldwide, AOTE-0707, MasterCard, 2007, pp. 1.

NACHA—The Electronic Payments Association, "A Guide to Understanding EFT Payments Processing", ACH Primer or Healthcare, pp. 1-20, 2011.

* cited by examiner

Fig. 3

Transactions

Search for [Transactions] [Deposits] [Fees]

Dates [08/21/2015] [08/21/2015]

| Date | Method | Name | Amt | Comment |
|---|---|---|---|---|
| 08/21/2015 | MC....9904 | StoneEagle | $48.40 | Claim: 02123X11234 |

Fig. 4

Transaction Detail

| | |
|---|---|
| Transaction ID: PI0005058000 | Date & Time Stamp: Aug 21st, 2015 07:41 am |
| Payment Type: Credit | Transaction Type: Sale |
| Cardholder Name: StoneEagle | Card Swiped: No |
| Card Number: ...9904 | Expiration Date: 10/2015 |
| Card Type: MasterCard | Recurring: No |
| Amount: $43.40 | Batch ID: 1410937250 |
| AVS Cardholder Billing Address: 111 W. Spring Valley Rd | AVS Cardholder Billing Address Match: Yes |
| AVS Cardholder Billing Zip Code: 75081 | AVS Cardholder Billing Zip Code Match: Yes |
| Response: Approved | Card Security Code Match: Not Supported |
| Security Features: No | Authorization Code: 129483 |
| Original Transaction ID: | Result Code: 0 |
| Comment: Claim 021230X11234 | |
| Commercial Card: No | |

REMITTANCE ADVICE

| | |
|---|---|
| Claim No.: 021230X11234 | Line: 0100 |
| Charged Total: 168.00 | Procedure: 70450 |
| Paid: 43.40 | Count: 1 |
| CoPay: 0 | Deduct: 0 |
| Discount: 0 | Carrier: XYZ Health |
| Patient: Robert M. Allen | |

360

 Print Remittance Advice    Save Remittance Advice    Configure File Format

Fig. 5

Transaction Detail

| | |
|---|---|
| Transaction ID: PI0005058000 | Date & Time Stamp: Aug 21st, 2015 07:41 am |
| Payment Type: Credit | Transaction Type: Sale |
| Cardholder Name: StoneEagle | Card Swiped: No |
| Card Number: ...9904 | Expiration Date: 10/2015 |
| Card Type: MasterCard | Recurring: No |
| Amount: $43.40 | Batch ID: 1410937250 |
| AVS Cardholder Billing Address: 111 W. Spring Valley Rd | AVS Cardholder Billing Address Match: Yes |
| AVS Cardholder Billing Zip Code: 75081 | AVS Cardholder Billing Zip Code Match: Yes |
| Response: Approved | Card Security Code Match: Not Supported |
| Security Features: No | Authorization Code: 129483 |
| Original Transaction ID: | Result Code: 0 |
| Comment Claim 021230X11234 | |
| Commercial Card: No | |

Remittance Advice is Available
Please Type Your PIN

360

[ **** ]  [ Submit ]

MERCHANT PORTAL SYSTEM WITH EXPLANATION OF BENEFITS

PRIORITY CLAIM

This application claims priority to U.S. Non-provisional patent application Ser. No. 14/833,853 filed Aug. 24, 2015 entitled "Check View System with Embedded Explanation of Benefits" which, in-turn claims priority to U.S. Non-provisional patent application Ser. No. 13/709,717 filed Dec. 10, 2012 having the same title, which further claims priority to U.S. Non-provisional patent application Ser. No. 13/495,492 filed Jun. 13, 2012 entitled "Integrated Payment and Explanation of Benefits Presentation Method for Healthcare Providers" which, in-turn, claims priority to U.S. Provisional Patent Application Ser. No. 61/653,175 filed May 30, 2012 also entitled "Integrated Payment and Explanation of Benefits Presentation Method for Healthcare Providers."

BACKGROUND OF THE INVENTION

1. Field of the Invention

This invention relates to electronic payment systems. More specifically, it relates to a method of using infrastructure that already exists in merchant card processor online portals to display sensitive protected health information such as explanation of benefits to healthcare providers for payment reconciliation.

2. Brief Description of the Related Art

Adjudication, payment and reconciliation of service provider claims against insurance carriers (particularly in the healthcare industry) consumes substantial time and resources. Third party administrators (herein "TPAs"), insurance companies, and large self-funded corporations (herein "Payers") adjudicate claims, compare them to a benefit plan and make the decision to write checks in payment for the claims. Currently, many payers are required to print checks and explanation of benefit (EOB) forms for delivery to the healthcare providers. The EOB lists the amount the healthcare provider billed the Payer's company and the amount the Payer's company paid on the claim. It may also list the contractual discount amount and the patient responsibility. If the claim is denied, the EOB will explain the reason for denial.

In an effort to streamline this process, Applicant developed a process described in U.S. Pat. No. 7,792,686, (succeeded by RE43904 and RE44748) the specification of which is incorporated herein by reference. The '686 patent discloses a method to deploy a single-load stored value card to pay medical service claims. Since there is a one-to-one relationship between the stored value card and the specific claim, reconciling the payment is made substantially more efficient.

SUMMARY OF THE INVENTION

The long-standing but heretofore unfulfilled need for reconciling secure and efficient adjudicated card payments to service providers is now met by a new, useful, and nonobvious invention.

In an embodiment of the invention, a TPA reviews a physician's claim to set a broken arm. The TPA works for a medical insurance company that covers the patient with the broken arm. Although the physician put in a claim for $1,000 the TPA determines that only $600 is covered under the patient's insurance policy. The TPA then authorizes payment of $600 to the physician but also includes an EOB which details the charges were covered and the charges that were denied. It is important for the physician to receive the EOB because it may be used to invoice the patient to cover their financial responsibility (i.e., the remaining $400 of the total $1,000 charge). The physician may submit the claim in an 837 standard format.

The ANSI ASC X12 837 standard can be used to submit healthcare claim billing information, encounter information, or both, from providers of healthcare services to payers, either directly or via intermediary billers and claims clearinghouses (TPAs). It can also be used to transmit healthcare claims and billing payment information between payers with different payment responsibilities where coordination of benefits is required or between payers and regulatory agencies to monitor the rendering, billing, and/or payment of healthcare services within a specific healthcare/insurance industry segment. For purposes of this standard, providers of healthcare products or services may include entities such as physicians, hospitals and other medical facilities or suppliers, dentists, and pharmacies, and entities providing medical information to meet regulatory requirements. The payer refers to a TPA that pays claims or administers the insurance product or benefit or both.

When the 837 submission is adjudicated by the TPA, the TPA returns an authorization to pay a certain amount which is explained in the EOB. An embodiment of the present invention operates as "middleware" between the sender of the EOB and the merchant account for the physician. The merchant account is the payment card vendor that enables the physician to accept credit cards, debit cards and other such payment card variants. The middleware decodes, parses or essentially separates the EOB from the payment authorization depending on the format. In some cases, the EOB data itself is sufficient to discern what should be paid to the provider. The middleware, embodied in a software application then requests a virtual payment card be generated for the payment amount authorized by the TPA. The virtual payment card includes a card account number (typically 16 digits), an authorized amount, an expiration date and a CVC security code. The virtual payment card cannot be processed for more than the amount authorized.

The decoded EOB is stored on a secure third party server such as database. Database server software is readily available under the brands of MICROSOFT SQL SERVER, ORACLE, IBM DB2 and the like.

Virtually all payment card merchant vendors offer online portals which allow the end-user to view transactions including deposits made from accepting payment cards. An important concept in the present invention is that the merchant vendors already have the online portal infrastructure in place. However, with traditional deposits there is no associated information regarding the EOB. However, in the instant invention, the merchant vendor is provided the EOB data from the middleware application in a number of embodiments including hyperlinks, iframes and the like.

BRIEF DESCRIPTION OF THE DRAWINGS

For a fuller understanding of the invention, reference should be made to the following detailed description, taken in connection with the accompanying drawings, in which:

FIG. 3 is an exemplary user interface showing processed card payments.

FIG. 4 is an exemplary user interface showing the details of an individual virtual card payment and an associated EOB delivered through an iframe.

FIG. 5 is an exemplary user interface showing the details of an individual virtual card payment and an end user request for a security PIN to access the EOB data through an iframe.

DETAILED DESCRIPTION OF THE PREFERRED EMBODIMENT

Figure 1:
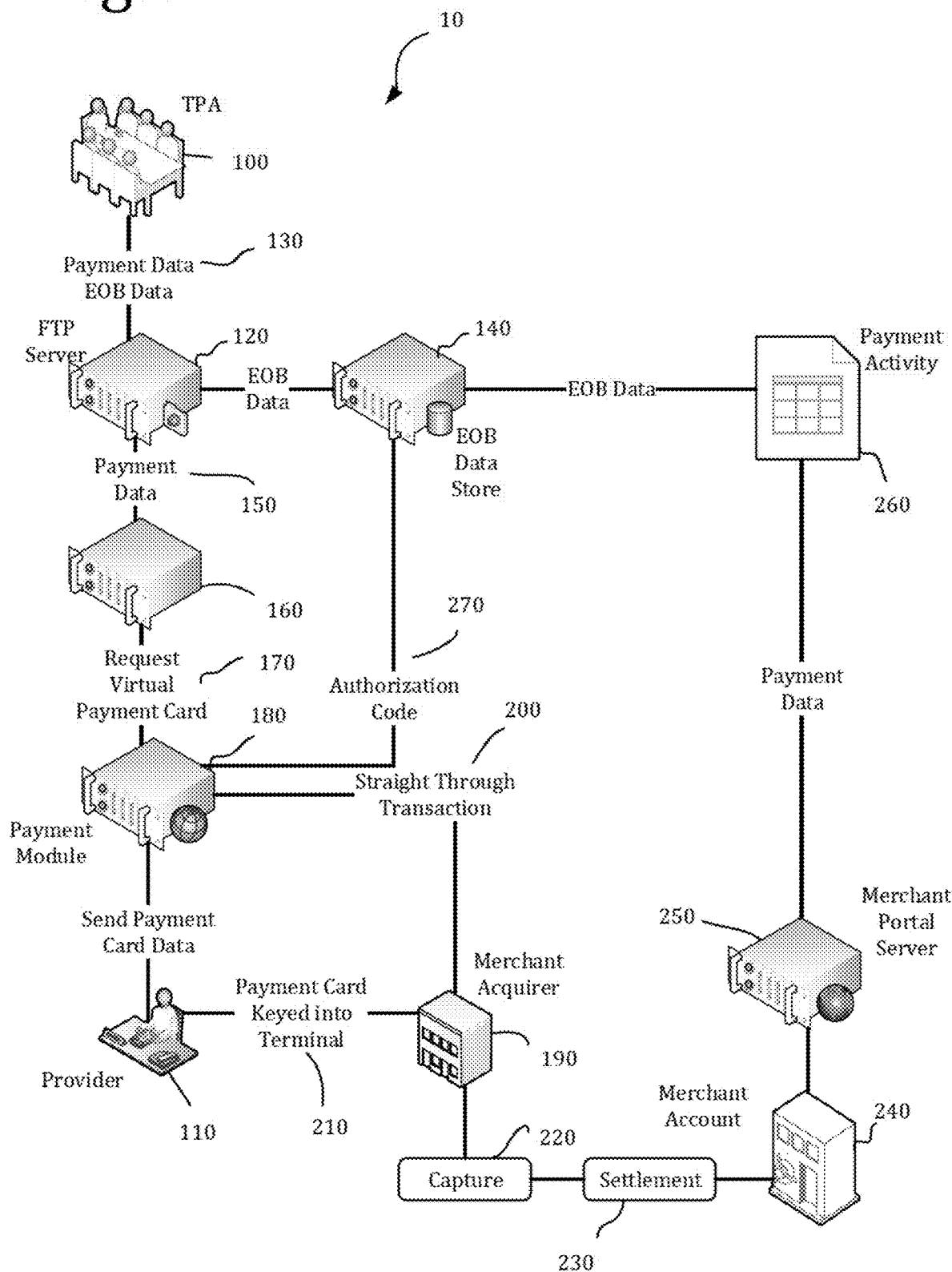
FIG. 1 is a diagrammatic view of an embodiment of the invention showing an exemplary workflow of information processing for presenting EOB data through an online merchant account portal.

The novel method is denoted as a whole in FIG. 1 by the reference numeral 10. Third party administrator (TPA) 100 adjudicates a claim submitted by provider 110. For illustrative purposes, provider 110 is a health care professional and the claim is for medical services rendered. However, the invention may be applied to other industries that provide remittance advice such as warranty repair and travel management. In the example, TPA 110 drops an electronic file 130 containing EOB and payment data into a remote store accessible by a payment intermediary. The payment data component indicates what should be paid out of the claim submitted by provider 110 and the EOB component is an explanation of what was paid under the claim. EOB is synonymous with explanation of payment (EOP) and also remittance advice. Generally, payment data is inherently within the EOB because by its nature, the EOB indicates what should be paid and what is denied under the claim. The amounts denied are generally billed as "patient responsibility" by the provider 110 later on. The EOB data is stored in an EOB data store 140 which may be a relational database such as MICROSOFT SQL SERVER or similar file storage means. It may be on premise or remotely located (e.g., cloud-based). While the EOB data is stored in the EOB data store 140 another process takes place. Payment data 150 for the claim is identified. This payment data 150 is the amount authorized by TPA 100 for payment to provider 110. Under an embodiment of the present invention, a middleware application 160 that is communicatively coupled to the FTP server 120 and the EOB data store 140 takes the payment data amount and payee identification within the payment data 150 and requests a virtual payment card be generated 170. The virtual payment card is preconfigured to the amount authorized by the TPA 100 for the claim payment and includes an expiration date and CVC security code. The expiration date may be a month or two from the date of generation as the card is generally considered to be a single-use instrument. This means that the card is intended to be run once by the provider 110 for payment of the entire authorized amount of the payment card. Should the provider attempt to run the card for an amount greater than that authorized the transaction will not be authorized. The virtual card account is then "recycled" for use at a later time once the transaction is processed.

A payment module 180 containing the virtual payment card data sends the payment card data either directly to provider 110 or sends it to the acquirer 190 for the provider's merchant account as a straight through transaction 200. If sent to the provider, the payment card data may be enumerated in a fax, email, hardcopy mailing or the like. The payment card data is keyed into a terminal 210 at the provider's place of business which then passes it to the merchant acquirer 190 for authorization, then capture 220 and eventually settlement 230.

Merchant account 240 for provider 110 provides transaction records through a merchant portal server 250 which is typically a secure website portal that the provider 110 logins into to reconcile payments received. Payment activity 260 is displayed generally in a table on a web page that allows the provider 110 to drill down into details of the transaction by clicking on those enumerated in a list sorted most often by date. The present invention provides EOB data from the EOB data store 140 in the detailed view of the merchant portal web page. In the embodiment shown in FIG. 1, the EOB data and the payment data are presented within the payment activity web page 260 from two sources, the EOB data store 140 and the merchant portal server 250 respectively.

One method of achieving this is through an iframe presented within the payment activity web page 260. An iframe (also known as an inline frame) is used to embed one document within another HTML document (base page). The base page delivered by merchant portal server 250 contains all the payment information typically found on a merchant account portal. However, the base page must know the path to which to point the iframe. This is the "SCR" value within the HTML markup and may simply consist of a well-formed URL path. An embodiment of the invention utilizes the authorization code 270 of the processed virtual card transaction as an identification value in the iframe path. For example, the authorization code may be hashed into a unique GUID value on both the intermediary side (the computer systems that receive TPA data and direct the payment card transmission) and also the merchant account side as they have possession of the authorization code as well. The path may be constructed out of a number of variables known directly or indirectly with each party so that a uniform resource locator (URL) path to the iframe may be set by the merchant portal server.

HTTPS is a protocol for security communications over the Internet. HTTPS consists of communication over Hypertext Transfer Protocol (HTTP) within a connection encrypted by Transport Layer Security or its predecessor, Secure Sockets Layer. The main motivation for HTTPS is authentication of the visited website and to protect the privacy and integrity of the exchanged data. In virtually all cases, the merchant portal server 250 will present its web page of payment activity 260 over HTTPS. Likewise, intermediary payment processor will deliver the EOB data in another HTTPS connection through the iframe. The intermediary does not have access to the first encrypted connection displaying payment data nor does the merchant portal have access to the second encrypted connecting displaying the EOB data. In this embodiment of the invention, each entity is isolated from each other and the only party viewing the combination of payment and EOB together is provider 110.

An advantage of the present invention is that the framework bifurcates two datasets having different but important security concerns. The EOB data is subject to the Health Insurance Portability and Accountability Act of 1996 (HIPAA). The HIPAA Privacy Rule regulates the use and disclosure of Protected Health Information (PHI) held by "covered entities" (generally, health care clearinghouses, employer sponsored health plans, health insurers, and medical service providers that engage in certain transactions.) The payment card data is subject to Payment Card Industry Data Security Standard (PCI DSS). PCI DSS is a proprietary information security standard for organizations that handle branded credit cards from the major card schemes including those under the brands VISA, MASTERCARD, AMERICAN EXPRESS, DISCOVER, and JCB. The current invention permits the merchant account to handle the PCI DSS payment data and still provide a pathway for the provider 110 to access the HIPAA data (EOB) in the context of the relevant payment. This provides a benefit to the provider 110 in that the EOB is linked to the payment made for the claim but also avoids the merchant account portal (which must handle all types of card transactions) to offload a substantial amount of HIPAA security concerns to the intermediary that coordinates payment on behalf of the TPA 100.

Figure 2:
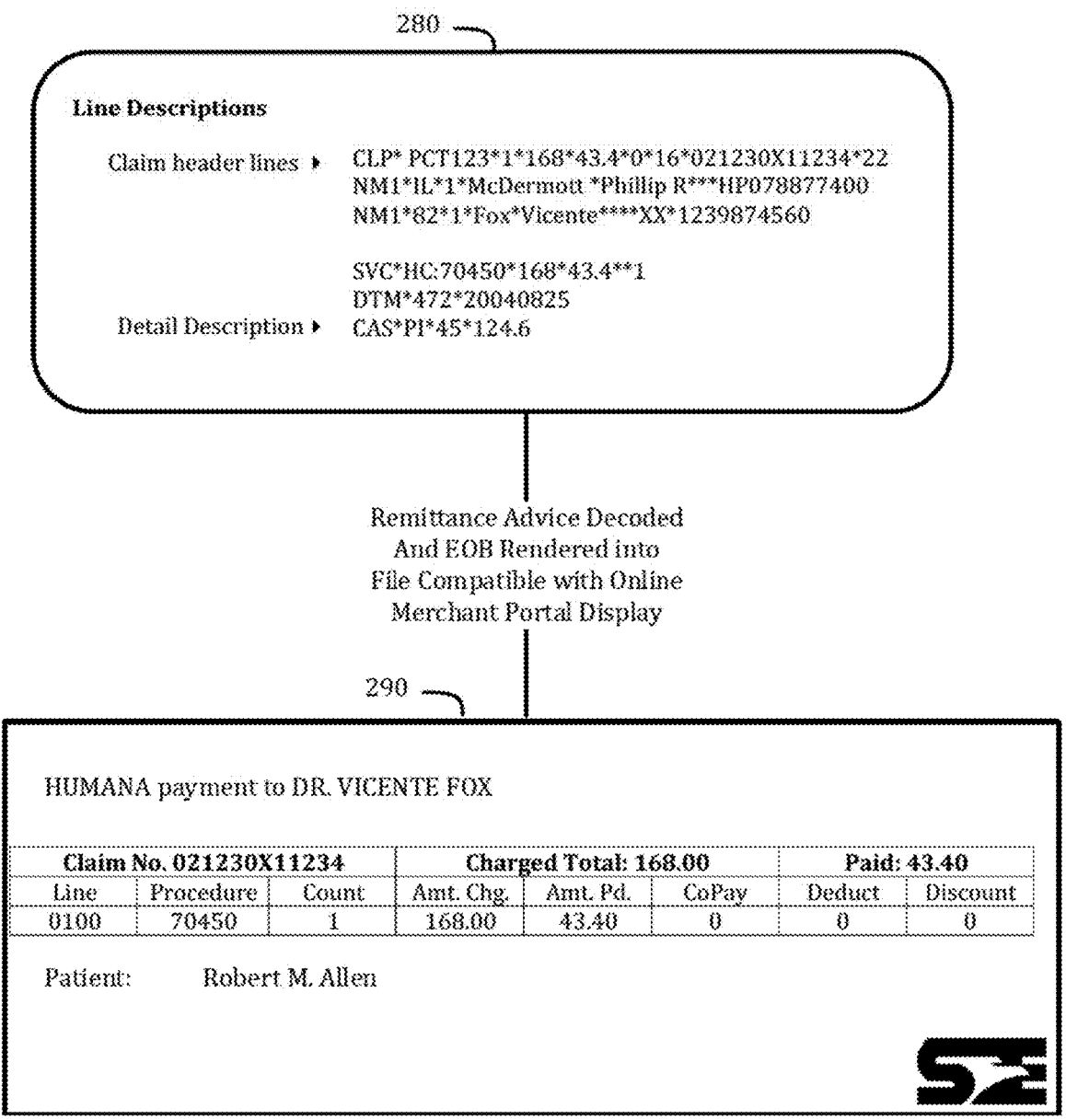
FIG. 2 is a conceptual view of a transaction set decoded and into a collection f fields for the EOB.

FIG. 2 shows a transaction set 280 containing EOB and payment data together. The transaction set is then decoded and EOB description 290 is generated and viewable through the payment activity web page 260 so that healthcare provider 110 can reconcile claims with payments and potentially invoice patients for amounts not covered by their insurance carrier as determined by TPA 100.

FIG. 3 shows an embodiment of a user interface 300 provided through payment activity web page 260. It should be noted that interface 300 could also be embodied in a proprietary client application such as an extension to a billing software such as sold under the brand QUICKBOOKS. Interface 300 may also be an application native to certain devices such as those under the IPAD, WINDOWS or ANDROID brands. For the sake of clarity, an abbreviated statement is shown in 300 having a transaction date 310, a method 320, a payee name 330, an amount 340 and a comment field 350. The transaction date 310 is the date upon which the payment card was processed, when funds were captured or when settlement occurred. Method 320 indicates the payment card used was a MASTERCARD-branded card and also provides the last four integers of the card PAN. The amount field 340 shows the deposit made was $48.40. This is preferably the gross deposit before interchange fees are deducted which makes reconciling easier for the provider 110 to perform. The comment field 350 indicates the claim identification that was paid. This field, and a combination of others may be used to link the EOB data record associated with the payment card transaction when presented together. In this example, when the end user selects the data row shown, a detailed view of the transaction is shown as exemplified in FIG. 4.

In FIG. 4, a transaction detail screen is shown providing additional details about the payment transaction. The cardholder in this case is StoneEagle which serves as the intermediary payment processor on behalf of the TPA. When a virtual card was requested for payment, it was generated in the name of the intermediary as a MASTERCARD-branded virtual card authorized for the amount of $43.40. As shown in the upper right column, the card was not swiped and (in this example) was keyed into the provider's card terminal. Alternatively, the intermediary payment processor might send the payment card data directly to the merchant acquirer wherein the provider is paid with the virtual card without having to take any manual steps. In such cases, the intermediary will likely generate some notification that it has been already been paid. Iframe 360 is embedded into the transaction detail interface, the iframe 360 pulled from a secure URL path to the associated EOB (or remittance advice) for the payment transaction. In this case, the total charged by provider was $168.00 but the TPA 100 adjudicated that insurance (XYZ HEALTH) was responsible for $43.40 of that amount for the patient. Options within the iframe 360 include printing the remittance advice, saving the remittance advice and/or configuring the file format of the remittance advice. The file format may be changed according to the various needs of the provider and the provider's software. The file format may be comma separated values, XML, or other file structures that may be imported and used by the practice management or billing software of the provider.

In FIG. 5, an embodiment of the invention password protects the iframe 360 with a PIN that provider is privy to. This may also be stored in the browser storage so that subsequent requests for the EOB data through iframe 360 do not require manual keying of the PIN into the interface.

In another embodiment of the invention, EOB data is passed onto the merchant portal service wherein it is presented within a single document including the payment data. There are a number of methods to achieving this. For example, the EOB data store checks to see that the IP address of the merchant portal server matches a white list of approved requesting addresses prior to delivering the EOB data. The EOB data may be provided as a web service wherein the merchant portal server receives an XML file or data stream from the intermediary processor responsive to a batch or on-demand request. If the merchant account provider does not wish to maintain the HIPAA-sensitive EOB data on its servers, it might prefer pulling the EOB data as a web service only when requested by the provider through the portal. Alternatively, a merchant account provider might request the EOB data from intermediary but keep it stored separately in a HIPAA-compliant database from the PCI DSS-compliant database holding the payment information.

In yet another embodiment of the invention a virtual private network (VPN) is established between merchant account portal and EOB data store wherein data exchanged between the two is secured.

Figure 6:
FIG. 6 is an exemplary user interface showing the details of a virtual card payment made for a plurality of patients with a hyperlink to detailed EOB data.

In FIG. 6, an interface is shown wherein a plurality of patient claims (Allen, Pfeifer and McDermott) are paid by a single virtual payment card in an amount totaling $2,215.94. The provider submitted claims for $5,058 total and the TPA found $2,215.94 payable. Therefore between the three patients listed below, the provider may bill them for $2,842.06 which was not covered by insurance. As there are three EOBs for the three patients, an individual hyperlink to each EOB is provided 370. However, the EOB data could be provided in a number of different ways. For example, all three EOB data sets could be loaded into the interface simultaneously and displayed on demand as the end user activates a view for each one. In the case of a web-based interface, this may be accomplished with a client-side script to make visible or hide various information panels containing the EOB content. The EOB data may also be pulled from the EOB data store by web service request using asynchronous JAVASCRIPT so there is no page refresh on the user interface.

In an alternative embodiment of the invention, the interface of FIG. 6 could show a single virtual card payment made for a plurality of claims relating to a single patient. As noted previously, the present invention may be applied not only to the health care industry but also other industries where payment of a claim by an intermediary is needed and remittance advice tied to the payment record through the merchant account system is advantageous. Other industries include, but are not limited to, vehicle warranty claims, home warranty claims, travel management claims and the like.

Glossary of Terminology

ACH Network: is an electronic network for financial transactions. The acronym ACH stands for automated clearing house. ACH processes large volumes of credit and debit transactions in batches. Rules governing ACH network operations are established by NACHA and the Federal Reserve.

ACH Operator: is an entity that acts as a central facility for the clearing, delivery and settlement of electronic money transfers through an ACH network or among participating depository financial institutions.

Authentication Code: is a secure code that links the EOB with the payment information across disparate computers and/or networks. For example, requiring the provider bank to supply a copy of an authentication code transmitted to the canonical or trusted point of contact for that identity before the EOB payment image file is transmitted to the designated endpoint.

Authorization: is permission obtained by the Originator from a Receiver to initiate entries through the ACH Network to the Receiver's account.

Computer display device: is a computer screen capable of displaying images and text. The computer display device may be a desktop display, laptop display, tablet display or portable device such as a smart phone.

Cross-Reference: means a data value that links one or more data fields to another. This may be a unique primary key (e.g. an integer or GUID) or may be one of the fields itself, a portion thereof or a derivative of one or more fields (e.g., hashed output value).

EDI 835: is a specification for the EDI Healthcare Claim Payment/Advice Transaction Set which can be used to make a payment, send an Explanation of Benefits (EOB), send an Explanation of Payments (EOP) remittance advice, or make a payment and send an EOP remittance advice only from a health insurer to a healthcare provider either directly or via a financial institution.

Electronic Data Interchange (EDI): is the exchange of computer-processable data in a standardized format between two enterprises.

Electronic Funds Transfer (EFT): is the electronic debit or credit of money from one account to another, either within a single financial institution or across multiple institutions, through computer-based systems.

Embedding: means inserting or including data from an alternate source of the default data on an interface or record.

GeoIP or Geolocation: computer geolocation can be performed by associating a geographic location with the Internet Protocol (IP) address, MAC address, RFID, hardware embedded article/production number, embedded software number (such as UUID, Exif/IPTC/XMP or modern steganography), Wi-Fi positioning system, or device GPS coordinates. Geolocation usually works by automatically looking up an IP address on a WHOIS service and retrieving the registrant's physical address. IP address location data can include information such as country, region, city, postal/zip code, latitude, longitude and time-zone. Deeper data sets can determine other parameters such as domain name, connection speed, ISP, language, proxies, company name, US DMA/MSA, NAICS codes, and home/business.

Health Insurance Portability and Accountability Act of 1996 (HIPPA, Title II): known as the Administrative Simplification (AS) provisions, requires the establishment of national standards for electronic healthcare transactions and national identifiers for providers, health insurance plans, and employers.

IP restrictions: are rules that limit the remote connections from one computer to another over a TCP/IP computer. An IP restriction typically grants or denies access to inbound and/or outbound connections based on a collection of four sets of integers and/or a range thereof.

Merchant Account: is account is a type of bank account that allows businesses to accept payments by payment cards, typically debit, stored value or credit cards. A merchant account is established under an agreement between an acceptor and a merchant acquiring bank for the settlement of payment card transactions. In some cases a payment processor, independent sales organization (ISO), or member service provider (MSP) is also a party to the merchant agreement. Whether a merchant enters into a merchant agreement directly with an acquiring bank or through an aggregator, the agreement contractually binds the merchant to obey the operating regulations established by the card associations such as those under the VISA and MASTER-CARD brands.

NACHA (association): is a non-profit association and private sector rulemaking body that supports the ACH Network integrity by managing its development, administration and governance. NACHA develops and enforces the NACHA Operating Rules.

NACHA (operating rules): are the body of work defining the requirements for all EFT transactions processed through the ACH Network. Financial Institutions, Originators, ACH Operators, and Third-Party Vendors using the ACH Network agree to be bound to the Rules.

Parse: is to read, generally through an I/O function an electronic file for information and values.

Participating Depository Financial Institution: is a financial institution that is authorized by applicable legal requirements to accept deposits, has been assigned a routing number by Accuity, and has agreed to be bound to the NACHA Operating Rules.

Payment image file: is an image file capable of being viewed by a computer display device. The image file may be bitmapped such as a PCX, TIF, GIF, JPG or PNG format. It may also contain vector or font data that is non-bitmapped which is supported by formats such as encapsulated postscript, PDF (portable document format by ADOBE) or the like.

Portal: a software application permitting remote access to records. In the case of a merchant account portal, this is typically a secure website that a vendor accesses through a web browser, logs in using a password and is able to view and download transactions relating to the vendor's merchant account, particularly charges processed by the vendor in payment of their goods and/or services. The portal is a useful tool for reconciling billing and accounts receivable data for the vendor.

Provider Bank: is the financial institution that receives payment for services rendered by the service provider (e.g., a physicians group, automobile repair facility or the like).

Routing/Transit Number: is a nine digit bank code, used in the United States, which appears on the bottom of negotiable instruments such as checks identifying the Financial Institution on which it was drawn.

Secure Sockets Layer (SSL): is a cryptographic protocol designed to provide communications security over a computer network. It uses X.509 certificates and hence asymmetric cryptography to authenticate the counterpart with whom it is communicating, and to negotiate a symmetric session key. For the purposes of this disclosure, Transport Layer Security (TLS) is an equivalent technology.

Service Provider: means a vendor providing goods or services under an agreement wherein at least a portion of the costs are anticipated to be covered. The service provider may be a health care provider, repair shop, travel agency or other vendor that submits a claim and expects at least partial payment thereof.

Storing: means saving data, values, fields and information to an electronically accessible storage device either local or remote to the software application executing the storage routine.

Third-Party Image Server: is a computer software server, generally coupled to a local and/or wide area network that receives, stores and transmits image files to authorized and authenticated computers and/or users. The server may be a single computer, a virtualized machine or multiple machines networked together such as a database server and file server operating together to store and fetch files responsive to T-SQL queries.

Transmission: means sending a data array, file, document or the like from one location to another.

Virtual Payment Card: is a payment card that may be processed under typical credit card infrastructure such as those branded VISA and MASTERCARD wherein a physical manifestation of the plastic card is not generated. A virtual payment card generally has a 16-digit account number, expiration date, security CVC code and an amount authorized to be charged.

Virtual Private Network (VPN): is a method for the extension of a private network across a public network, such as the Internet. It enables users to send and receive data across shared or public networks as if their computing devices were directly connected to the private network, and thus are benefiting from the functionality, security and management policies of the private network. A VPN is created by establishing a virtual point-to-point connection through the use of dedicated connections, virtual tunneling protocols, or traffic encryption.

The advantages set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense.

What is claimed is:

1. A method for displaying on an electronic device a user interface for displaying an explanation of benefits (EOB) and contemporaneously displaying virtual payment card deposits in a user interface of a computer application portal to a service provider, the method comprising the steps of:
    displaying a user interface on a computer screen, the user interface having an iframe embedded therein, wherein the user interface is displayed within a merchant account application portal administered by the merchant account of the service provider;
    receiving an electronic adjudicated claim file, the electronic file containing EOB data;
    storing the EOB data in an EOB data store, the EOB data having payment information including a payment obligation amount and a provider identity;
    decoding the EOB data to render the EOB data embeddable within the user interface;
    storing a cross-reference value that links the payment information and the EOB;
    generating a request by the application for a virtual payment card in an amount equal to that authorized by the adjudicated claim file, the virtual payment card including an account number, an expiration date and an amount value;
    electronically transmitting the virtual payment card as a straight through transaction to the service provider or to a merchant acquirer for the service provider, wherein the virtual payment card is processed in the authorized amount as payment to the service provider;
    displaying the EOB data within the iframe embedded within the user interface of the portal, such that the EOB data is retrieved using the cross-reference value and displayed within the user interface; and
    responsive to an inquiry by the service provider through the user interface of the online portal for the payment information for the adjudicated claim, displaying, within the user interface, the embedded EOB data linked to the payment information based on the cross reference, whereby the payment information is retrieved from the merchant account and the explanation of benefits is retrieved from the EOB data store.

2. The method of claim 1 further comprising the step of establishing IP restrictions for the portal connections wherein connections not within a whitelist by a portal for EOB data are refused by the application.

3. The method of claim 1 further comprising the step of establishing a virtual private network connection between the application and the portal.

4. The method of claim 1 further comprising the step of capturing by the application, an authorization code generated responsive to processing the virtual payment card and using the authorization code as an authentication factor for displaying the embedded EOB data within the online portal to the service provider.

5. A method for displaying on a computer screen a user interface for displaying an explanation of benefits (EOB) and contemporaneously displaying virtual payment card deposits in a user interface of a computer application portal to a service provider, the method comprising the steps of:
    displaying a user interface on a computer screen, the user interface having an iframe embedded therein, wherein the user interface is displayed within a merchant account application portal administered by the merchant account of the service provider;
    receiving an electronic adjudicated claim file, the electronic file containing EOB data;
    storing the EOB data in an EOB data store, the EOB data having payment information including a payment obligation amount and a provider identity;
    decoding the EOB data to render the EOB data embeddable within the user interface;
    storing a cross-reference value that links the payment information and the EOB;
    generating a request by the application for a virtual payment card in an amount equal to that authorized by the adjudicated claim file, the virtual payment card including an account number, an expiration date and an amount value;
    electronically transmitting the virtual payment card as a straight through transaction to the service provider or to a merchant acquirer for the service provider, wherein the virtual payment card is processed in the authorized amount as payment to the service provider;
    displaying the EOB data within the iframe of the user interface with a second secure socket layer connection within the portal used for displaying payment card deposits such that the EOB data is delivered to the user interface at the direction of the application responsive to a service request by portal using a uniform resource locator path within iframe, the path derived using the cross-reference value; and responsive to an inquiry by the service provider through the user interface of the online portal for the payment information for the adjudicated claim, displaying, on the user interface, the embedded EOB data through the iframe in context with the payment information, whereby the payment information is retrieved from the merchant account and the explanation of benefits is retrieved from the EOB data store.

6. The method of claim 5 further comprising the step of establishing IP restrictions for the portal connections wherein connections not within a whitelist by a portal for EOB data are refused by the application.

7. The method of claim 5 further comprising the step of establishing a virtual private network connection between the application and the portal.

8. The method of claim 5 further comprising the step generating a GUID value as a cross-reference between the EOB and the payment data wherein the GUID value forms part of the path to the iframe source.

9. The method of claim 8 wherein the GUID value is a first authentication factor for the iframe source path and further comprising the step of capturing by the application an authorization code generated by the processing of the virtual payment card, the authorization code forming a second authentication factor whereby the iframe source path includes both the GUID value and the authorization code.

10. The method of claim 5 further comprising the step of requiring a passcode propriety to the provider, keyed in through the iframe prior to displaying the EOB data associated with the payment.

11. The method of claim 5 further comprising the steps of:
retrieving the address of the provider by the application;
retrieving the IP address of the provider accessing the portal by the application;
referencing the IP address against a geoIP location table,
verifying that the IP addresses is within a geographic boundary threshold of the address known for the provider; and
displaying the EOB data through the iframe upon successful verification that the entity accessing the portal is doing so through a computer connected to the Internet within the geographic boundary threshold.

12. A method for displaying on an electronic device a user interface for displaying an explanation of benefits (EOB) and contemporaneously displaying virtual payment card deposits in a user interface of a computer application portal to a service provider, the method comprising the steps of:

displaying a user interface on a computer screen, the user interface having an iframe embedded therein, wherein the user interface is displayed within a merchant account application portal administered by the merchant account of the service provider;

receiving an electronic adjudicated claim file, the electronic file containing EOB data;

storing the EOB data in an EOB data store, the EOB data having payment information including a payment obligation amount and a provider identity;

decoding the EOB data to render the EOB data embeddable within the user interface;

storing a cross-reference value that links the payment information and the EOB;

generating a request by the application for a virtual payment card in an amount equal to that authorized by the adjudicated claim file, the virtual payment card including an account number, an expiration date and an amount value;

electronically transmitting the virtual payment card as a straight through transaction to the service provider or to a merchant acquirer for the service provider, wherein the virtual payment card is processed in the authorized amount as payment to the service provider;

providing a unique uniform resource locator (URL) string associated with a processed virtual card payment to the merchant account application portal administered by the merchant account of the service provider, whereby a reference in the portal linking to the URL is displayed in context with processed virtual card payment transaction record viewable in the user interface; and displaying within the iframe of the user interface, the EOB data at the URL provided and through a second secure socket layer connection responsive to a request by a user accessing the portal on behalf of the provider.

13. The method of claim 12 wherein the portal is accessible through a web browser.

14. The method of claim 12 wherein the portal is accessible through a proprietary client-side application run by the provider.

15. The method of claim 14 wherein the proprietary client-side application retrieves a plurality of processed virtual card transactions from the merchant account and associated EOB records together in batch and populates a data store within the client-side application with the transaction and EOB data.

* * * * *